United States Patent [19]
Richard et al.

[11] Patent Number: 6,004,540
[45] Date of Patent: *Dec. 21, 1999

[54] PHOTOPROTECTIVE/COSMETIC COMPOSITIONS COMPRISING SULFONAMIDO-FUNCTIONAL POLYORGANOSILOXANES/ POLYORGANOSILANES

[75] Inventors: Hervé Richard, Villepinte; Madeleine Leduc, Paris; Alain Lagrange, Couvray, all of France

[73] Assignee: Societe L'Oreal S.A., Paris, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/880,747

[22] Filed: Jun. 23, 1997

Related U.S. Application Data

[63] Continuation of application No. 08/559,941, Nov. 17, 1995, abandoned.

[30] Foreign Application Priority Data

Nov. 17, 1994 [FR] France ................................ 94-13771

[51] Int. Cl.$^6$ ................................................ A61K 7/021
[52] U.S. Cl. ...................... 424/59; 424/70.122; 556/425; 556/418; 528/28; 514/938
[58] Field of Search ..................... 556/425, 418; 528/28; 424/59, 70.122; 514/938

[56] References Cited

U.S. PATENT DOCUMENTS

| | | | |
|---|---|---|---|
| 2,957,781 | 10/1960 | Bailey et al. | 117/33.3 |
| 4,668,505 | 5/1987 | Grollier et al. | 424/47 |
| 5,061,479 | 10/1991 | Grollier et al. | 424/47 |

FOREIGN PATENT DOCUMENTS

| | | |
|---|---|---|
| 0335777 | 10/1989 | European Pat. Off. . |
| 0389338 | 9/1990 | European Pat. Off. . |
| 0392883 | 10/1990 | European Pat. Off. . |
| 2157174 | 10/1985 | United Kingdom . |
| 92/19625 | 11/1992 | WIPO . |

Primary Examiner—Margaret G. Moore
Attorney, Agent, or Firm—Burns, Doane, Swecker & Mathis, L.L.P.

[57] ABSTRACT

Topically applicable sunscreen/cosmetic compositions well suited for enhanced photoprotection of human skin and/or hair against the damaging effects of UV-A and UV-B irradiation, particularly solar radiation, comprise a photoprotecting effective amount of a novel sulfonamido-functional polyorganosiloxane/polyorganosilane having one of the formulae (1) to (3):

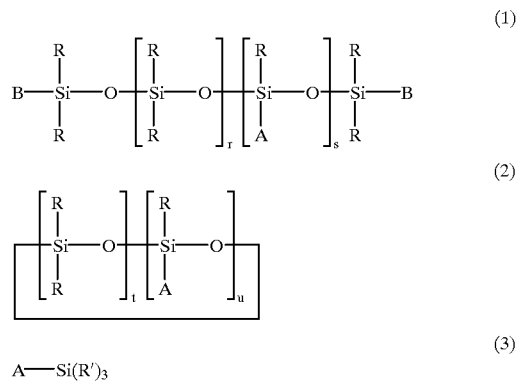

$A$—$Si(R')_3$ (3)

wherein A is a monovalent benzylidenecamphor radical which comprises a sulfonamido-functional bridging group, which is bonded directly to a silicon atom, and which has the formula. (4.1)

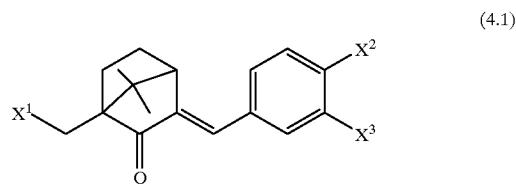

27 Claims, No Drawings

PHOTOPROTECTIVE/COSMETIC COMPOSITIONS COMPRISING SULFONAMIDO-FUNCTIONAL POLYORGANOSILOXANES/ POLYORGANOSILANES

This application is a continuation, of application Ser. No. 08/559,941, filed Nov. 17. 1995, now abandoned.

CROSS-REFERENCE TO COMPANION APPLICATIONS

Our copending applications Ser. No. 08/541,983, now U.S. Pat. No. 5,663,270, filed Oct. 10, 1995, and Ser. No. 08/555,334, now U.S. Pat. No. 5,569,451, and Ser. No. 08/555,046, now U.S. Pat. No. 5,610,257, both filed Nov. 8, 1995, and Ser. No. 08/560,489, now U.S. Pat. No. 5,587,151, and Ser. No. 08/559,940, now U.S. Pat. No. 5,827,509 both filed concurrently herewith; each of the above applications is assigned to the assignee hereof.

BACKGROUND OF THE INVENTION

1. Technical Field of the Invention

The present invention relates to novel compounds comprising short-chain, linear or cyclic diorganosiloxanes or triorganosilanes having at least one specific sunscreening substituent bonded thereto via a sulfonamido-functional bridging group.

This invention also relates to novel cosmetic compositions for topical application comprising said sulfonamido-functional polyorganosiloxanes/polyorganosilanes, for the photoprotecion of the skin and/or hair against ultraviolet radiation (such compositions hereinafter sometimes simply designated "sunscreen," "sunscreen/cosmetic" or "photoprotective/sunscreen" compositions).

2. Description of the Prior Art

It is known to this art that light radiation of wavelengths of from 280 nm to 400 nm promotes tanning of the human epidermis, and that irradiation of wavelengths of from 280 to 320 nm, i.e, UV-B irradiation, causes erythema and skin burns which can impair the development of a natural tan; hence, such UV-B radiation must thus be screened from the skin.

It is also known to this art that UV-A radiation, of wavelengths of from 320 to 400 nm, which tans the skin, also adversely affects it, in particular in the event of sensitive skin or skin constantly exposed to solar radiation. UV-A irradiation causes, in particular, a loss in the elasticity of the skin and the appearance of wrinkles, promoting a premature aging thereof. Such irradiation promotes triggering of the erythematous reaction or enhances this reaction in certain individuals, and may even be the source of phototoxic or photoallergic reactions. Thus, it is desirable to also screen out UV-A radiation.

A wide variety of compounds intended for the photoprotection (UV-A and/or UV-B) of human skin are known to this art.

Most of these are aromatic compounds displaying an absorption of UV radiation in the region from 280 to 315 nm or in the region of from 315 to 400 nm, or else in both of these regions together. They are, more often than not, formulated in sunscreen compositions as oil-in-water emulsions (namely, a cosmetically acceptable vehicle, carrier or diluent comprising an aqueous continuous dispersing phase and an oily discontinuous dispersed phase) which contain, at various concentrations, one or more traditional lipophilic and/or hydrophilic organic sunscreen compounds comprising an aromatic function suitable for selectively absorbing harmful or deleterious UV radiation. These sunscreen compounds (and the amounts thereof) are selected as a function of the desired specific sun protection factor (the specific protection factor (SPF) being expressed mathematically by the ratio of the irradiation time required to attain the erythemogenic threshold with the UV screening agent to the time required to attain the erythemogenic threshold in the absence of UV screening agent.)

Other than their sunscreen activity, these compounds having anti-UV properties must also display good cosmetic characteristics in the compositions comprised thereof, good solubility in common solvents, and especially fats such as oils and greases, and also good resistance to water and to perspiration (durability).

Among such prior art aromatic compounds, p-aminobenzoic acid derivatives, benzylidenecamphor derivatives and especially 3-benzylidenecamphor derivatives, cinnamic acid derivatives and benzotriazole derivatives are particularly representative. However, certain of these compounds do not display all of the properties required for an acceptable UV screening agent in sunscreen compositions. In particular, their intrinsic screening activity may be insufficient, their solubility in the different formulations employed for photoprotection is not always sufficiently good (fat solubility in particular), they may not possess sufficient stability to light (photostability) and they may also display resistance to water and to sweat. It is also desirable that these sunscreen compositions do not penetrate into the skin.

Thus, in the particular case of sunscreen compounds of the benzotriazole or 3-benzylidenecamphor type, derivatives thereof have been prepared which have improved properties, especially in respect of their fat solubility and their cosmetic character, by effecting bonding of the benzotriazole or 3-benzylidenecamphor screening group via grafting (hydrosilylation), by means of an alkylene or alkyleneoxy bridging group, onto a macromolecular chain of the silicone (organopolysiloxane) type. Such derivatives are described in EP-A-0,392,883 (benzotriazole) and EP-A-0,335,777 (3-benzylidenecamphor), both assigned to the assignee hereof, and are generally denominated "silicone screening agents," but the fat-solubility of these compounds can still be inadequate and, furthermore, in order to provide satisfactory sunscreen properties, it is often necessary to employ relatively large amounts of these photoprotective polymers, resulting in poor cosmetic properties in respect of the formulations comprised thereof.

SUMMARY OF THE INVENTION

Accordingly, a major object of the present invention is the provision of novel sulfonamido-functional silicone/silane sunscreen compounds which display improved properties, in particular in respect of their solubility in fats, as well as regards their cosmetic properties.

Thus, it has now unexpectedly been determined that by grafting, in particular via hydrosilylat-ion, one or more specific 3-benzylidenecamphor, benzotriazole, benzophenone or benzimidazole derivatives, onto a particular linear or cyclic silicone chain or a particular silane via a sulfonamido--functional bridging group, novel silicone/silane sunscreen compounds are prepared which avoid or conspicuously ameliorate the above disadvantages and drawbacks of the prior art silicone sunscreens, said novel compounds displaying, in particular, very high sunscreen activity, both in the UV-A range and in the UV-B range, very good solubility in the common organic solvents and notably in fatty substances such as oils, and also excellent cosmetic properties, rendering same particularly well suited for formulation into photoprotective/cosmetic compositions for protecting the skin and/or the hair against the damaging or deleterious effects of ultraviolet radiation.

Briefly, the present invention features novel compounds having one of the following formulae (1) to (3):

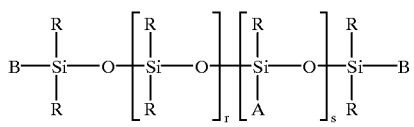
(1)

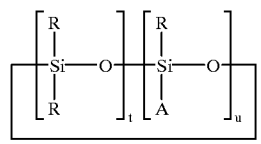
(2)

A—Si(R')₃ (3)

in which the radicals R, which may be identical or different, are each a $C_1-C_{10}$ alkyl, phenyl or 3,3,3-trifluoropropyl radical, at least 80% by number of the radicals R being methyl radicals; the radicals B, which may be identical or different, are each a radical R or a radical A as defined below; the radicals R', which may be identical or different, are each a $C_1-C_8$ alkyl radical or a phenyl radical; r is an integer ranging from 0 to 50, inclusive, and s is an integer ranging from 0 to 20, inclusive, with the proviso that, if s is zero, then at least one of the two radicals B is a radical A; u is an integer ranging from 1 to 6, inclusive, and t is an integer ranging from 0 to 10, inclusive, with the proviso that t+u is equal to or greater than 3; and the radical A is a monovalent radical bonded directly to a silicon atom and which has one of the following formulae (4.1) to (4.4):

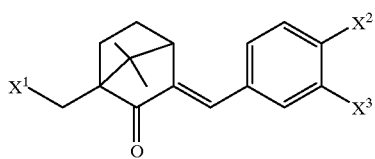
(4.1)

in which $X^1$ is a hydrogen atom or a divalent radical —Y— having the following formula (5):

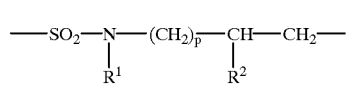
(5)

wherein $R^1$ is a hydrogen atom or a $C_1-C_4$ alkyl or hydroxyalkyl radical; $R^2$ is a hydrogen atom or a $C_1-C_6$ alkyl or $C_1-C_6$ alkoxy radical; p is an integer ranging from 1 to 10, inclusive; and the —CH₂— endgroup is directly bonded to a silicon atom; $X^2$ and $X^3$, which may be identical or different, are each a hydrogen or halogen atom, a $C_1-C_4$ alkyl or alkoxy radical, a divalent radical —Y— or a radical Z having the following formula (6):

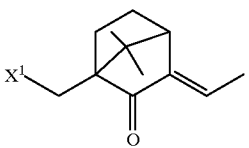
(6)

with the proviso that the radicals $X^2$ and $X^3$ may together form an alkylidenedioxy group in which the alkylidene moiety contains 1 or 2 carbon atoms; and with the further provisos that, in formula (4.1), one of the three radicals $X^1$, $X^2$ and $X^3$ is necessarily a divalent radical —Y—, and each of the other two radicals cannot be a divalent radical —Y—, that, if $X^1$ is a hydrogen atom, $X^2$ and $X^3$ are then necessarily different and neither is a radical Z, that, if $X^1$ is a divalent radical —Y—, $X^2$ and $X^3$ cannot simultaneously be a radical Z, and that, if $X^1$ is a hydrogen atom and $X^3$ is a divalent radical —Y—, then $X^2$ is preferably other than a hydrogen atom;

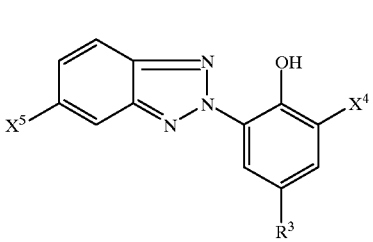
(4.2)

in which $X^4$ is a hydrogen atom, a $C_1-C_8$ alkyl radical or a divalent radical —Y—; $X^5$ is a hydrogen or halogen atom, a $C_1-C_4$ alkyl or alkoxy radical, or a divalent radical —Y—; $R^3$ is a $C_1-C_8$ alkyl radical, with the proviso that, in formula (4.2), one of the two radicals $X^4$ and $X^5$ is necessarily a divalent radical —Y— and the other cannot be a divalent radical —Y—;

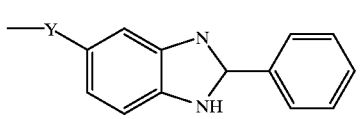
(4.3)

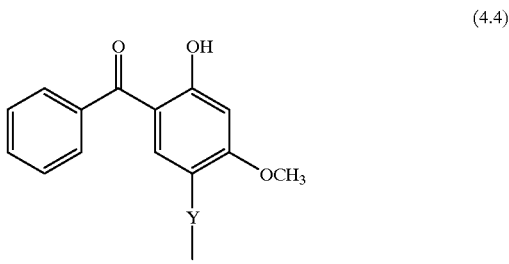
(4.4)

wherein —Y— is as defined above.

DETAILED DESCRIPTION OF BEST MODE AND PREFERRED EMBODIMENTS OF THE INVENTION

More particularly according to the present invention, in the above formulae (1) to (3), A is thus a sunscreening moiety selected from among 3-benzylidenecamphor compounds (formula 4.1), benzotriazoles (formula 4.2), benzimidazoles (formula 4.3) and benzophenones (formula 4.4) which, after bonding to the starting short silicone chain or to the starting silane, imparts absorbing properties to the compounds of linear diorganosiloxane type (formula (1)), or of cyclic diorganosiloxane type (formula (2)), or of triorganosilane type (formula (3)), with respect to ultraviolet radiation within a wavelength region which may range from 280 to 400 nm. As indicated above, and as is apparent from the definitions of the aforesaid formulae (4.1) to (4.4), this screening moiety group necessarily comprises at least one sulfonamide functional group (formula 5) which is provided by the linking or bridging structural unit which couples the screening moiety to the silicone chain or to the silane. One of the great advantages of the compounds of the invention, and more particularly of those in which the screening moiety A has the structural formula (4.1) or structural formula (4.2), is that, depending on the nature and/or the position of the various substituents borne by the screening moiety A, photoprotective agents are provided which are either purely UV-A sunscreens, or, to the contrary, purely UV-B sunscreens, with particularly high extinction coefficients.

Also as is apparent from the definitions given above, the coupling of the linking radical —$SO_2$—$N(R^1)$—$(CH_2)_p$—$CH(R^2)$—$CH_2$— (namely, the divalent radical —Y— of formula (5) comprising the sulfonamide function) to a 3-benzylidenecamphor nucleus thus bonds said moiety to a silicon atom of the silicone backbone or of the silane; this substitution can be effected at any one of the positions occupied by the radicals $X^1$, $X^2$ and $X^3$, the —$SO_2$— endgroup being bonded to the 3-benzylidenecamphor moiety and the —$CH_2$— endgroup being bonded to a silicon atom of the silicone backbone or of the silane. Still in the specific event that the screening moiety is a 3-benzylidenecamphor compound, it will be appreciated that this moiety may optionally comprise two linking or bridging structural units (this is effectively possible when $X^1$ is a divalent radical —Y— and when, simultaneously, $X^2$ or $X^3$ is a radical Z comprising this same divalent radical —Y—) and may thus be bonded to two different silicone backbones, or nuclei, or to two different silyl structural units.

In the event of a screening moiety of benzotriazole type (formula 4.2), or of benzimidazole type (formula 4.3), or of benzophenone type (formula 4.4), there can only be a single bridging structural unit —Y—; this structural unit is located at one of the positions occupied by the radicals $X^4$ and $X^5$ in the case of benzotriazoles, and in well-defined positions in the other cases.

In the above formulae (1) to (3), the alkyl radicals can be linear or branched and are advantageously selected from among methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The preferred alkyl radicals R, R' and B according to the invention are methyl, ethyl, propyl, n-butyl, n-octyl and 2-ethylhexyl radicals. Even more preferably, the radicals R, R' and B are all methyl radicals. As regards the halogen atoms, these are advantageously selected from among chlorine, fluorine and bromine, and are preferably chlorine. The alkoxy radicals are advantageously selected from among methoxy, ethoxy, n-propoxy, isopropoxy, n-butoxy and isobutoxy radicals.

Among the compounds of the above formulae (1) to (3), preferred are those corresponding to formula (1) or to formula (2), namely, linear or cyclic short-chain diorganosiloxanes.

Among the linear or cyclic diorganosiloxanes according to the present invention, preferred are the random derivatives or well-defined block derivatives having at least one, and even more preferably all, of the following characteristics and definitions (except for the instances of mutual exclusions indicated above for the three radicals $X^1$, $X^2$ and $X^3$ when the screening moiety is a 3-benzylidenecamphor derivative, or for the two radicals $X^4$ and $X^5$ when the screening moiety is a benzotriazole):

R is alkyl and, even more preferably, is methyl,

B is alkyl and, even more preferably, is methyl (in the case of the linear compounds of formula (1)), r ranges from 0 to 3, inclusive; s ranges from 0 to 3, inclusive (in the case of the linear compounds of formula (1)), t+u ranges from 3 to 5 (in the case of the cyclic compounds of formula (2)), $R^1$ is H, $R^2$ is H or methyl, p ranges from 1 to 3 inclusive, $X^1$ is H or —Y—, $X^2$ is H. methyl, methoxy, —Y— or Z.

$X^3$ is H or —Y—, $X^4$ is tert-butyl or —Y—, $X^5$ is H or —Y—, $R^3$ is methyl or tert-butyl.

The preferred compounds of formulae (1) to (3) according to the present invention are those comprising screening moieties A selected from among the 3-benzylidenecamphor derivatives having the above formula (4.1).

To prepare the silicone sunscreen agents of formulae (1) and (2), a standard hydrosilylation reaction (Method 1) is employed, i.e.:

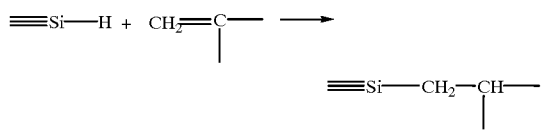

starting from the corresponding silicone in which, for example, all of the radicals A are hydrogen atoms. This starting silicone will hereinafter be designated the derivative containing SiH; the SiH groups may be present in the silicone backbone and/or at the ends of the silicone chain. These derivatives containing SiH are well known compounds in the silicone industry and are generally commercially available. They are described, for example, in U.S. Pat. Nos. 3,220,972, 3,697,473 and 4,340,709.

This derivative containing SiH may thus be represented, depending on the particular case, either by the following formula (1a):

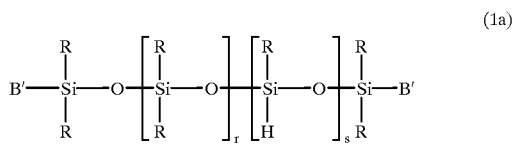

in which R, r and s are as defined above in respect of the formula (1) and the radicals B', which may be identical or different, are selected from among the radicals R and a hydrogen atom, or by the following formula (2a):

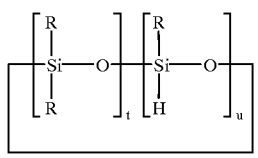

(2a)

in which R, t and u are as defined above in respect of the formula (2).

A conventional hydrosilylation reaction is thus carried out on this derivative containing SiH of formula (1bis) or (2bis), in the presence of a catalytically effective amount of a platinum catalyst, depending on the particular case (i.e., depending on the nature of the screening moiety to be grafted), either with an organic 3-benzylidenecamphor compound having the following formula (4.1a):

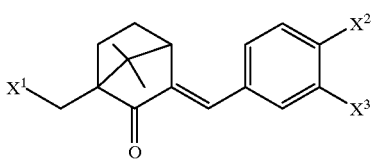

(4.1a)

in which $X^1$, $X^2$ and $X_3$ are as defined above for formula (4.1), except that one of these three radicals, instead of representing a saturated divalent radical —Y— of above formula (5), is, in this event, the corresponding unsaturated homologous monovalent radical —Y' having the following formula (5a):

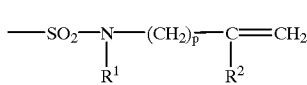

(5a)

in which $R^1$, $R^2$ and p are as defined above in respect of the formula (5);

or with an organic benzotriazole compound having the following formula (4.2a):

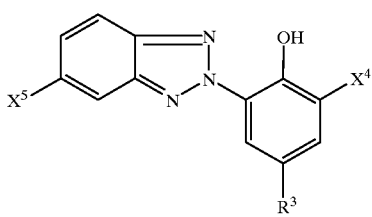

(4.2a)

in which $X^4$ and $X^5$ are as defined above in respect of the formula (4.2), except that one of these two radicals, instead of representing a saturated divalent radical —Y— of the above formula (5), is, in this case, the corresponding unsaturated homologous monovalent radical —Y' of the above formula (5a);

or with an organic benzimidazole compound having the following formula (4.3a):

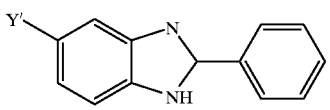

(4.3a)

in which Y' is the unsaturated monovalent radical of the above formula (5a), a homolog of the saturated diradical —Y— of formula (4.3);

or with an organic benzophenone compound having the following formula (4.4a):

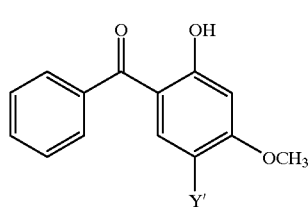

(4.4a)

in which Y' is the unsaturated monovalent radical of the above formula (5a), the homolog of the saturated diradical —Y— of formula (4.4).

Exemplary compounds of formula (4.1a) according to the present invention include, in particular:

(a) N-allyl-4-(4,7,7-trimethyl-3-oxobicyclo-[2.2.1] hept-2-ylidenemethyl)benzenesulfonamide;

(b) N-allyl-C-[3-(4-methoxybenzylidene)-7,7-dimethyl-2-oxobicyclo[2.2.1]hept-1-yl] methanesulfonamide;

(c) N-allyl-C-(3-benzylidene-7,7-dimethyl-2-oxobicyclo[2.2.1]hept-1-yl)methanesulfonamide;

(d) N-allyl-C-(3-benzo[1,3]dioxol-5-ylmethylene-7,7-dimethyl-2-oxobicyclo[2.2.1]hept-1-yl) methanesulfonamide;

(e) N-(2-methyl-allyl)-4-(4,7,7-trimethyl-3-oxobicyclo [2.2.1]hept-2-ylidenemethyl)benzenesulfonamide.

The compounds of formulae (4.1a) to (4.4a) above may themselves be prepared in conventional manner (see in particular, FR-A-2,529,887 as regards the compounds of formula 4.1a) by reacting (i) the corresponding unsaturated amine having the formula (5b):

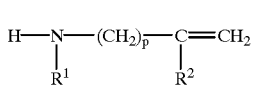

(5b)

in which $R^1$, $R^2$ and p are as defined above in respect of formula (5), with (ii) the sulfonyl chloride of the screening moiety which it is desired to graft, namely, therefore:

either a sulfonyl chloride of an organic 3-benzylidenecamphor compound selected from among those of the following formula (4.1b):

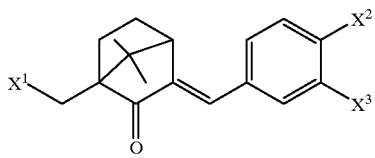
(4.1b)

in which $X^1$, $X^2$ and $X^3$ are as defined above in respect of formula (4.1), except that one of these three radicals, instead of representing a divalent radical —Y— of the above formula (5), is, in this case, the monovalent radical —SO$_2$Cl;

or a sulfonyl chloride of an organic benzotriazole compound selected from among those of the following formula (4.2b):

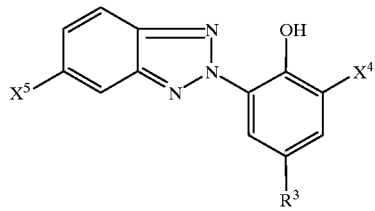
(4.2b)

in which $X^4$ and $X^5$ are as defined above in respect of formula (4.2), except that one of these two radicals, instead of Representing a saturated divalent radical —Y— of the above formula (5), is, in this case, the monovalent radical —SO$_2$Cl;

or a benzimidazolesulfonyl chloride of the following formula (4.3b):

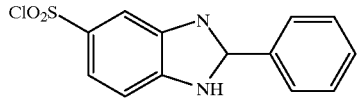
(4.3b)

or a benzophenonesulfonyl chloride of the following formula (4.4b):

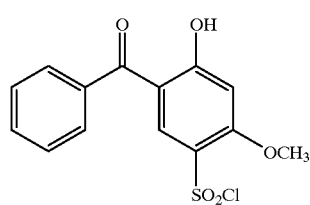
(4.4b)

All of the above sulfonyl chlorides may themselves be prepared conventionally, by reacting, in a solvent such as DMF, (i) the corresponding sodium sulfonates (namely, compounds of formulae (4.1a), (4.2a), (4.2a) and (4.4a), in which the radical —Y' is —SO$_3$Na) with (ii) thionyl chloride (see, in particular, the aforementioned FR-A-2,529, 887).

The platinum catalysts used to carry out the hydrosilylation reaction between the compounds of the above formula (1a) or (2a) with the compounds of the above formulae (4.1a) to (4.4a) are well known and widely described in the literature. Exemplary thereof are, in particular, the complexes of platinum and an organic compound described in U.S. Pat. Nos. 3,159,601, 3,159,602, 3,220,972 and European Patent Applications EP-A-0,057,459, EP-A-0,188,978 and EP-A-0,190,530 and the complexes of platinum and vinyl organopolysiloxane described in U.S. Pat. Nos. 3,419, 593, 3,377,432 and 3,814,730. To react the compounds of formula (1a) or (2a) with the compounds of formulae (4.1a) to (4.4a), an amount of platinum catalyst, calculated as weight of platinum metal, ranging from 5 to 600 ppm, preferably from 10 to 200 ppm, based on the weight of compounds of formula (1a) or (2a) is generally employed. The hydrosilylation reaction may be carried out in bulk or in a volatile organic solvent such as toluene, heptane, xylene, tetrahydrofuran or tetrachloroethylene. It is generally desirable to heat the reaction mixture to a temperature ranging from 60° to 120° C. for the period of time required for the reaction to be driven to completion. The compound of formula (1a) or (2a) may be added dropwise to the compound of formula (4.1a), (4.2a), (4.3a) or (4.4a) in solution in an organic solvent containing the catalyst. The compound of formula (1a) or (2a) and the compound of formula (4.1a) (or (4.2a) to (4.4a), respectively) may also be added simultaneously to a suspension of catalyst in an organic solvent. It is preferred to monitor that the reaction is complete by assaying the residual SiH using alcoholic potassium hydroxide, followed by removal of the solvent, for example by distillation under reduced pressure. The crude oil obtained may be purified, for example by cascading same through an absorbent column of silica.

As regards the preparation of the screening agents of triorganosilane type of formula (3) given above, the process may be carried out as indicated above, again by a hydrosilylation reaction, between a starting silane of formula (R')$_3$SiH (formula (3a), in which R' has the same definition as for the compound of formula (3)), and an organic derivative selected from among (depending on the screening moiety desired for the final product) an organic 3-benzylidenecamphor compound of the above formula (4.1a), an organic benzotriazole compound of the above formula (4.2a), an organic benzimidazole compound of the above formula (4.3a), and an organic benzophenone compound of the above formula (4.4a).

Another synthetic route (Method 2) which is suitable for the preparation of the silicone sunscreen agents of formulae (1) and (2) entails reacting compounds corresponding, respectively, to formula (1) or to formula (2) in which all of the radicals A are replaced by the following radical of formula (5c):

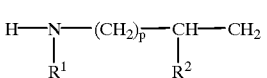
(5c)

in which $R^1$, $R^2$ and p are as defined above in respect of the formula (5).

The radicals of formula (5c) may be present in the silicone backbone or chain and/or at the ends of the silicone chain. These starting aminosiloxane compounds may thus be represented either by the following formula (1b) (linear aminosiloxane derivative):

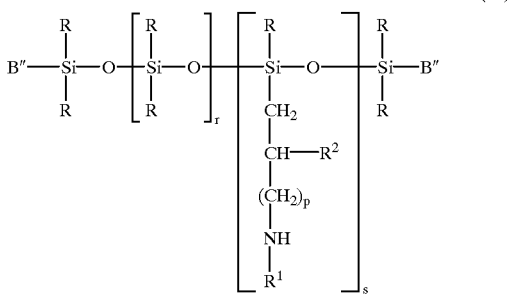

(1b)

in which R, r and s are as defined above in respect of the formula (1) and the radicals B'', which may be identical or different, are selected from among the radicals R and the radical of formula (5c), or by the following formula (2b) (cyclic aminosiloxane derivative):

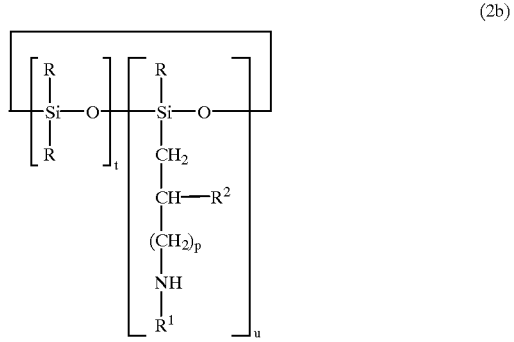

(2b)

in which R, t and u are as defined above in respect of the formula (2).

The aminosiloxane derivatives of formula (1b) or (2b) above are well known compounds in the silicone industry and are generally commercially available. They are, in addition, described, in particular, in DE-A-3,702,631, as regards the short chain silicones.

These aminosiloxane derivatives are then reacted with the sulfonyl chloride of the screening moiety which it is desired to graft, namely, therefore:

either a sulfonyl chloride of an organic 3-benzylidenecamphor derivative selected from among those of the above formula (4.1b);

or a sulfonyl chloride of an organic benzotriazole derivative selected from among those of the above formula (4.2b);

or a sulphonyl chloride of a benzophenone of formula (4.4b) defined above.

Compared with the silicone photoprotective agents of the prior art, and in particular with those described in the aforementioned EP-A-0,392,883 and EP-A-0,335,777, the silicone sunscreen agents according to the invention thus exhibit one or more essential structural differences which are the source of their exceptional properties, and, in particular: the silicone chains onto which the selected screening moieties are grafted, are firstly much shorter; next, the selected screening moiety still comprises a sulfonamide function.

Also as indicated above, the compounds of formulae (1) to (3) above exhibit excellent intrinsic screening activity with respect to UV-A and UV-B ultraviolet radiation, depending upon the particular chemical structure thereof. In addition, taking account of their highly liposoluble nature, the compounds of formulae (1) to (3) may be used in high concentrations, thereby imparting very high specific protection factors to the final compositions; moreover, they distribute themselves uniformly in standard cosmetic vehicles comprising at least one fatty phase or at least one cosmetically acceptable organic solvent, and may thus be applied to the skin or hair to form an effective protective film. Too, their cosmetic properties are very good, namely, in particular, compared with the silicone screening agents of the prior art, these products are less sticky and render the skin or hair softer.

Thus, the present invention also features cosmetic compositions comprising, in a cosmetically acceptable vehicle, carrier or diluent, preferably including at least one fatty phase or at least one organic solvent, an effective photoprotective amount of at least one compound of the above formulae (1) to (3).

The compounds of formulae (1) to (3) are advantageously present in proportions ranging from 0.1% to 20% by weight, and preferably from 0.5% to 10% by weight, relative to the total weight of the composition.

The cosmetic compositions of the invention may be used as compositions for protecting the human epidermis or hair against ultraviolet rays, as sunscreen compositions or as makeup products.

These compositions may, in particular, be in the form of a lotion, a thickened lotion, a gel, a cream, an ointment, a milk, a powder or a solid stick and may optionally be packaged as an aerosol, as a foam, a mousse or a spray.

They can contain the usual cosmetic adjuvants and additives, such as fats and fatty substances, organic solvents, silicones, thickeners, softeners, emollients, complementary sunscreens, anti-foaming agents, moisturizing or hydrating agents, fragrances and perfumes, preservatives, surfactants, fillers, sequestering agents, anionic, cationic, nonionic or amphoteric polymers or mixtures thereof, propellants, basifying or acidifying agents, colorants, dyes, pigments or nanopigments, in particular those designed to provide a complementary photoprotective effect by physically blocking out ultraviolet radiation, or any other ingredient customarily used in cosmetics, especially for the production of sunscreen compositions.

Exemplary of the organic solvents are the lower alcohols and polyols, such as ethanol, isopropanol, propylene glycol, glycerol and sorbitol.

The fats or fatty substances can comprise of an oil or wax or mixtures thereof, fatty acids, fatty acid esters, fatty alcohols, petrolatum, paraffin, lanolin, hydrogenated lanolin or acetylated lanolin. The oils may be selected from among animal, vegetable, mineral or synthetic oils and, in particular, hydrogenated palm oil, hydrogenated castor oil, liquid petrolatum, liquid paraffin, purcellin oil, volatile or non-volatile silicone oils, and isoparaffins.

When the cosmetic composition according to the invention are used for protecting the human epidermis against the deleterious or damaging effects of UV irradiation or as sunscreen compositions, they are advantageously formulated as a suspension or dispersion in solvents or fatty substances, or, alternatively, in the form of an emulsion (in particular of O/W or W/O type, but preferably of O/W type) such as a cream or a milk, or of a vesicle dispersion, or as an ointment, a salve, a gel, a solid stick or an aerosol foam. The emulsions may additionally contain anionic, nonionic, cationic or amphoteric surface-active agents.

When the cosmetic compositions according to the invention are used for the photoprotection of the hair, they can be formulated as a shampoo, a lotion, a gel or rinse, to be applied before or after shampooing, before or after dyeing or bleaching, before, during or after permanent-waving or straightening of the hair, or as a styling or treatment lotion or gel, a blow-drying or hair-setting lotion or gel, a hair lacquer, a permanent-waving or hair-straightening composition, or a composition for dyeing or bleaching the hair.

When the cosmetic compositions according to the invention are used as makeup products for the eyelashes, the eyebrows, the skin or the hair, such as a skin-treatment cream, a foundation, a lipstick, an eye shadow, a blush, an eyeliner, a mascara or a coloring gel., they can be formulated in solid or pasty, anhydrous or aqueous form, such as oil-in-water or water-in-oil emulsions, suspensions or gels.

The cosmetic treatment of the skin or hair to protect same against the deleterious effects of ultraviolet radiation, in particular solar radiation, comprising topically applying to the skin or hair an effective amount of a sunscreen/cosmetic composition as described above, or of a compound of the above formulae (1, to (3).

In order to further illustrate the present invention and the advantages thereof, the following specific examples are given, it being understood that same are intended only as illustrative and in nowise limitative.

EXAMPLE 1

This example relates to the preparation (according to Method 1) of N-3-[1,3,3,3-tetramethyl-1-[(trimethylsilyl) oxy]disiloxanyl]propyl-4-(4,7,7-trimethyl)-3-oxobicyclo [2.2.1]hept-2-ylidenemethyl)benzenesulphonamide, namely, a compound in accordance with the present invention, having the structural formula:

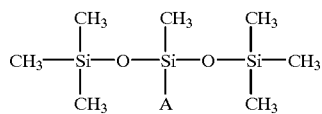

in which A is the radical:

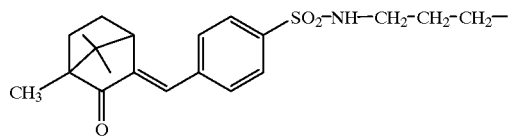

(this compound has formula (1) in which R=B=CH$_3$; r=0, s=1; X$^1$=X$^3$=H; R$^1$=R$^2$=H; p 1)

(a) First stage:

34.2 g of the sodium salt of 4-(4,7,7-trimethyl-3-oxobicyclo[2.2.1]hept-2-ylidenemethyl)benzenesulfonic acid and 200 ml of dimethylformamide were introduced into a 500 ml reactor. 13 g of thionyl chloride were then introduced dropwise. The reaction mixture was then stirred at room temperature for 2 hours. Allylamine (6.3 g) and then triethylamine (11.1 g) were next added dropwise and stirring was maintained for 3 hours. The reaction mixture was poured into 300 ml of water. The solid obtained was drained and then dried and, after purification, 21.4 g of N-allyl-4-(4,7,7-trimethyl-3-oxobicyclo[2.2.1]hept-2-ylidenemethyl) benzenesulfonamide, having the following characteristics, were recovered:

White powder
m.p.: 131° C.
Elemental analysis:
theoretical C 67.09 H 7.04 N 3.66
   S 8.88
  found C 66.82 H 7.01 N 3.90
   S 8.92

(b) Second stage:

17.97 g of the compound obtained above and 50 ml of toluene were introduced into a reactor. The mixture was heated to 80° C. under nitrogen. The hydrosilylation catalyst (complex containing 3–3.5% of Pt in cyclovinylmethylsiloxane, marketed by Huls under the trademark Petrarch PC085, 100 μl) was added, followed by 11.24 g of heptamethyltrisiloxane.

After 4 hours at 80° C. under nitrogen, the reaction medium was concentrated and chromatography was carried out on silica under pressure (eluent: heptane/EtOAc 97/3). 21.8 g of the desired final compound, having the following characteristics, were thus obtained:

White powder
m.p.: 73° C.
Elemental analysis:
  theoretical C 55.72 H 8.14
    N 2.41 S 5.51
    Si 14.48
  found C 55.88 H 8.09
    N 2.62 S 5.49
    Si 14.28

The UV absorption characteristics (measured in ethanol) of this compound were as follows:

$\lambda_{max}$: 295 nm $\epsilon_{max}$: 28,900

This compound is thus a very effective sunscreen which is active in the UV-B range.

EXAMPLE 2

Following the same procedure as that given in Example 1, four other compounds in accordance with the present invention (compounds A to D) were prepared, all having the general formula (1) and comprising the same silicone-containing skeleton or backbone:

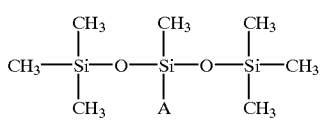

but in each case comprising a screening unit A of different structure.

The results obtained are reported in the following Table:

TABLE

| Structural Unit A | UV (ethanol) $\lambda_{max}$ | $\epsilon_{max}$ | Elemental Analysis (1) = calculated (2) = found |
|---|---|---|---|
| A ![structure A] | 322 nm | 25,950 | (1): C 54.95 H 8.07, N 2.29, S 5.24, Si 13.77 (2): C 54.95, H 8.08, N 2.42, S 4.99, Si 13.54 |
| B ![structure B] | 293 nm | 23,225 | (1): C 55.72, H 8.14, N 2.41, S 5.51, Si 14.48 (2): C 55.85, H 8.17, N 2.33, S 5.39, Si 13.93 |
| C ![structure C] | 337 nm | 21,220 | (1): C 53.72, H 7.57, N 2.24, S 5.12, Si 13.46 (2): C 53.84, H 7.60, N 1.94, S 4.96, Si 13.07 |
| D ![structure D] | 295 nm | 28,970 | (1): C 56.43 H 8.26, N 2.35, S 5.38, Si 14.14 (2): C 56.37, H 8.25, N 2.37, S 5.44, Si 13.85 |

Compounds A, B, C and D are thus very effective sunscreens which are active, respectively, in the WV-A range, the UV-B range, the UV-A range and the UV-B range.

EXAMPLE 3

This example relates to the preparation (according to method 2) of bis-N-{3-[1,3,3,3-tetramethyl-1-[(trimethylsilyl)oxy]disiloxanyl]propyl}-3,3'-terephthalylidene-10,10'-dicamphorsulfonamide, namely, a compound in accordance with the present invention, having the structural formula:

4 g of the disodium salt of 3,3'-terephthalylidene-10,10'-dicamphorsulfonic acid and 16 ml of dimethylformamide were introduced into a reactor. 1.1 ml of thionyl chloride were then added dropwise thereto and stirring was maintained for half an hour. This heterogeneous mixture was added portionwise to a mixture of triethylamine (3.04 g) and 1-amino-1-[1,3,3,3-tetramethyl-3-[(trimethylsilyl)-oxy]disiloxanyl]propane (4.2 g). The reaction mixture was maintained at room temperature for 3 hours and was then poured into 100 ml of ice-cold water and was lastly extracted with dichloromethane. The organic phase was dried over sodium sulfate and concentrated. After chromatography on silica

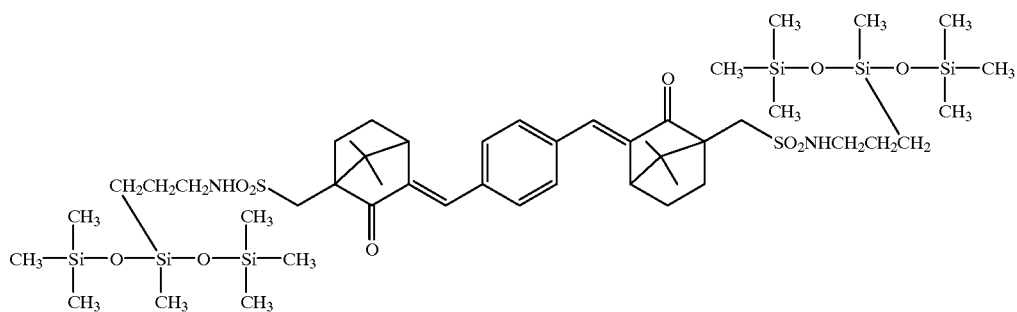

(this compound has formula (1) in which R=B=CH$_3$; r=0; s=1; X$^1$=—Y— with R$^1$=R$^2$=H and p=1; X$^2$=Z; X$^3$=H).

(eluent: CH$_2$Cl$_2$), 3 g of the desired final compound, having the following characteristics, were thus obtained:

White powder
m.p.: 176°–177° C.
Elemental analysis:
theoretical C 52.23 H 8.00
N 2.65 S 6.06
Si 15.93
found C 52.92 H 8.12 N 2.43
S 5.94 Si 15.37

The UV absorption characteristics (measured in CHCl$_3$) of this compound were as follows:

$\lambda_{max}$: 344 nm $\in_{max}$: 47,100

This compound is thus a very effective sunscreen which is active in the UV-A range.

EXAMPLE 4

This example relates to the preparation (according to method 2) of 2-phenyl-1H-benzimidazole-5-{N-3-[1,3,3,3-tetramethyl-1-[(trimethylsilyl)oxy]-disiloxanylipropyl}sulfonamide, namely, a compound in accordance with the present invention, having the structural formula:

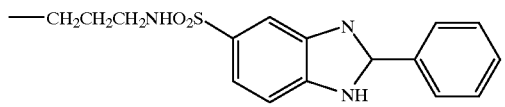

in which A is the radical:

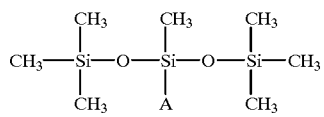

(this compound has formula (1) in which R=B=CH$_3$; r=0; s=1; R$^1$=R$^2$=H and p=1)

100 ml of dry dichloromethane, 60 ml of triethylamine and 67 g of heptamethylaminopropyltrisiloxane (compound having formula (1b) in which R=B"=CH$_3$; r=0; s=1; R$^1$=R$^2$=H; p=1) were introduced into a reactor. 23.4 g of 2-phenyl-1H-benzimidazole-5-sulfonyl chloride were added to this mixture, portionwise over half an hour at room temperature. The heterogeneous mixture obtained was then heated at 60° C. for 3 hours. After cooling, the reaction mixture was poured into 300 ml of water. After extraction with dichloromethane and purification by chromatography on silica (eluent: heptane/CH$_2$Cl$_2$ 50/50), 8 g of the desired final compound, having the following characteristics, were obtained:

White powder
m.p.: 169°–170° C.

The UV absorption characteristics (measured in ethanol) of this compound were as follows:

$\lambda_{max}$: 305 nm $\in_{max}$: 29,500

$\lambda_{max}$: 317 nm $\in_{max}$: 19,675

This compound is thus a very effective sunscreen which is active in the UV-B range.

EXAMPLE 5

Following the same procedure as that given in Example 4, another compound in accordance with the present invention was prepared, having the following structural formula:

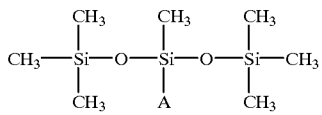

in which A is the radical:

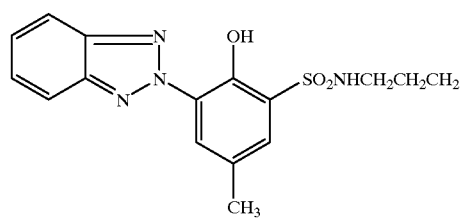

(this compound has formula (1) in which R=B=CH$_3$; r=0; s=1; X$^4$=—Y— with R$^1$=R$^2$=H and p=1; X$^5$=H; R$^3$=methyl).

The UV absorption characteristics (measured in ethanol) of this compound were as follows:

$\lambda_{max}$: 294 nm $\in_{max}$: 12, 100

$\lambda_{max}$: 325 nm $\in_{max}$: 7,300

This compound is thus a very effective sunscreen which is active in the UV-B and UV-A ranges.

EXAMPLE 6

A photoprotective/sunscreen formulation in accordance with the invention was prepared in the form of a sunscreen cream:

| | |
|---|---|
| (a) Compound of Example 1 | 5 g |
| (b) Mixture of cetylstearyl alcohol and cetylstearyl alcohol oxyethylenated with 33 mol of EO ("SINNOWAX AO" marketed by Henkel) | 7 g |
| (c) Mixture of non-self-emulsifiable glyceryl mono- and distearate | 2 g |
| (d) Cetyl alcohol | 1.5 g |
| (e) C$_{12}$—C$_{15}$ alkyl benzoate ("FINSOLV TN" marketed by Witco) | 20 g |
| (f) Polydimethylsiloxane | 1.5 g |
| (g) Glycerol | 17.5 g |
| (h) Fragrance, preservative qs | |
| (i) Water qs | 100 g |

This cream was formulated according to the standard techniques for the preparation of emulsions, by dissolving the screening agent in the fatty phase containing the emulsifying agents, heating this fatty phase to about 70°–80° C. and adding, with vigorous stirring, the water which had been heated to the same temperature. Stirring was maintained for 10 to 15 minutes and, after permitting this formulation to cool with moderate stirring, the fragrance and preservatives were then finally added at about 40° C.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A sulfonamido-functional polyorganosiloxane/polyorganosilane compound having one of the formulae (1) to (3):

(1)
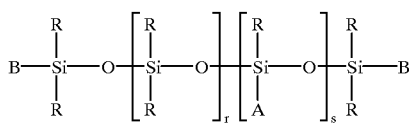

(2)
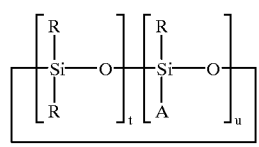

(3)
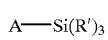

in which the radicals R, which are identical or different, are each a $C_1$–$C_{10}$ alkyl, phenyl or 3,3,3-trifluoropropyl radical, at least 80% by number of the radicals R being methyl radicals; the radicals B, which may be identical or different, are each a radical R or a radical A as defined below; the radicals R', which may be identical or different, are each a $C_1$–$C_8$ alkyl radical or a phenyl radical; r is an integer ranging from 0 to 50, inclusive, and s is an integer ranging from 0 to 20, inclusive, with the proviso that, if s is zero, then at least one of the two radicals B is a radical A; u is an integer ranging from 1 to 6, inclusive, and t is an integer ranging from 0 to 10, inclusive, with the proviso that t+u is equal to or greater than 3; and the radical A is a monovalent radical bonded directly to a silicon atom and which has one of the following formula (4.1)

(4.1)
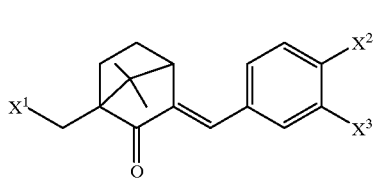

in which $X^1$ is a hydrogen atom or a divalent radical —Y— having the following formula (5):

(5)
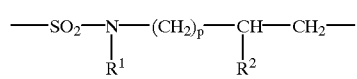

wherein $R^1$ is a hydrogen atom or a $C_1$–$C_4$ alkyl or hydroxyalkyl radical; $R^2$ is a hydrogen atom or a $C_1$–$C_6$ alkyl or $C_1$–$C_6$ alkoxy radical; p is an integer ranging from 1 to 10, inclusive; and the —$CH_2$— endgroup is directly bonded to a silicon atom; $X^2$ and $X^3$, which may be identical or different, are each a hydrogen or halogen atom, a $C_1$–$C_4$ alkyl or alkoxy radical, a divalent radical —Y— or a radical Z having the following formula (6):

(6)
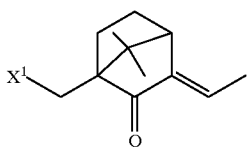

with the proviso that the radicals $X^2$ and $X^3$ may together form an alkylidenedioxy group in which the alkylidene moiety contains 1 or 2 carbon atoms; and with the further provisos that, in formula (4.1), one of the three radicals $X^1$, $X^2$ and $X^3$ is necessarily a divalent radical —Y—, and each of the other two radicals cannot be a divalent radical —Y—, that, if $X^1$ is a hydrogen atom, $X^2$ and $X^3$ are then necessarily different and neither is a radical Z, and that, if $X^1$ is a divalent radical —Y—, $X^2$ and $X^3$ cannot simultaneously be a radical Z.

2. A polyorganosiloxane/polyorganosilane compound as defined by claim 1, having the formula (1).

3. A polyorganosiloxane/polyorganosilane compound as defined by claim 1, having the formula (2).

4. A polyorganosiloxane/polyorganosilane compound as defined by claim 1, having the formula (3).

5. A polyorganosiloxane/polyorganosilane compound as defined by claims 2 or 3, wherein the formulae (1) and (2), the radicals R are alkyl radicals.

6. A polyorganosiloxane/polyorganosilane compound as defined by claim 5, said radicals R being methyl, ethyl, propyl, n-butyl, n-octyl or 2-ethylhexyl radicals.

7. A polyorganosiloxane/polyorganosilane compound as defined by claim 6, said radicals R being methyl radicals.

8. A polyorganosiloxane/polyorganosilane compound as defined by claim 2, wherein formula (1) the radicals B are alkyl radicals.

9. A polyorganosiloxane/polyorganosilane compound as defined by claim 8, said radicals B being methyl, ethyl, propyl, n-butyl, n-octyl or 2-ethylhexyl radicals.

10. A polyorganosiloxane/polyorganosilane compound as defined by claim 9, said radicals B being methyl radicals.

11. A polyorganosiloxane/polyorganosilane compound as defined by claim 2, wherein formula (1), r ranges from 0 to 3 and s ranges from 0 to 3.

12. A polyorganosiloxane/polyorganosilane compound as defined by claim 1, wherein formula (2), t+u ranges from 3 to 5.

13. A polyorgosilanoxane/polyorganosilane compound as defined by claim 4, wherein formula (3), the radicals R' are methyl, ethyl, propyl, n-butyl, n-octyl or 2-ethylhexyl radicals.

14. A polyorganosiloxane/polyorganosilane compound as defined by claim 13, said radicals R' being methyl radicals.

15. A polyorganosiloxane/polyorganosilane compound as defined by claim 1, wherein the formulae (1) to (3), in a divalent radical —Y—, p ranges from 1 to 3.

16. A polyorganosiloxane/polyorganosilane compound as defined by claim 1, wherein the formulae (1) to (3), in a divalent radical —Y—, $R^1$ is hydrogen.

17. A polyorganosiloxane/polyorganosilane compound as defined by claim 1, wherein the formulae (1) to (3), in a divalent radical —Y—, $R^2$ is hydrogen or a methyl radical.

18. A polyorganosiloxane/polyorganosilane compound as defined by claim 1, wherein the formulae (1) to (3), A is a radical having the formula (4.1).

19. A polyorganosiloxane/polyorganosilane compound as defined by claim 18, wherein the formulae (1) to (3), $X^2$ is hydrogen, a methyl or methoxy radical, or a divalent radical —Y—.

20. A polyorganosiloxane/polyorganosilane compound as defined by claim 18, wherein the formulae (1) to (3), $X^3$ is hydrogen or a divalent radical —Y—.

21. The compound of claim 1, wherein if $X^1$ is a hydrogen atom and $X^3$ is a divalent radical —Y—, then $X^2$ is not a hydrogen atom.

22. A topically applicable sunscreen/cosmetic composition adopted for the photoprotection of human skin and/or hair, comprising a photoprotectin effective amount of a polyorganosiloxane/polyorganosilane compound as defined by claim 1, in a cosmetically acceptable vehicle, carrier or diluent therefor.

23. The sunscreen/cosmetic composition as defined by claim 22, said cosmetically acceptable vehicle, carrier or diluent comprising at least one fatty phase or at least one organic solvent.

24. The sunscreen/cosmetic composition as defined by claim 22, comprising an oil-in-water or water-in-oil emulsion.

25. The sunscreen/cosmetic composition as defined by claim 22, comprising from 0.1% to 20% by weight of said photoprotecting compound.

26. A method for protecting human skin and/or hair against the deleterious effects of ultraviolet irradiation, comprising topically applying thereto an effective amount of the sunscreen/cosmetic composition as defined by claim 22.

27. A method for protecting human skin and/or hair against the deleterious effects of solar radiation, comprising topically applying thereto an effective amount of the sunscreen/cosmetic composition as defined by claim 22.

* * * * *